United States Patent [19]

Young

[11] Patent Number: 4,518,703

[45] Date of Patent: May 21, 1985

[54] CRYSTALLINE SILICA CATALYSTS

[75] Inventor: Dean A. Young, Yorba Linda, Calif.

[73] Assignee: Union Oil Company of California, Los Angeles, Calif.

[21] Appl. No.: 447,477

[22] Filed: Dec. 6, 1982

Related U.S. Application Data

[62] Division of Ser. No. 157,211, Jun. 9, 1980, Pat. No. 4,433,187, which is a division of Ser. No. 12,868, Feb. 16, 1979, Pat. No. 4,270,017.

[51] Int. Cl.³ .................. B01J 21/06; B01J 21/16; B01J 27/00
[52] U.S. Cl. ................................ 502/63; 502/80; 502/214; 502/232; 502/242; 502/244; 502/250; 502/251; 502/256; 502/262; 502/263
[58] Field of Search ............ 252/455 Z; 502/80, 214, 502/232, 242, 244, 250, 259, 262, 263, 256, 251, 63

[56] References Cited

U.S. PATENT DOCUMENTS

| | | |
|---|---|---|
| Re. 28,398 | 4/1975 | Chen et al. . |
| Re. 29,857 | 12/1978 | Argauer et al. . |
| Re. 29,948 | 3/1979 | Dwyer . |
| 3,493,341 | 3/1970 | Page et al. . |
| 3,506,400 | 4/1970 | Eberly et al. . |
| 3,702,886 | 11/1972 | Argauer et al. . |
| 3,729,409 | 4/1973 | Chen . |
| 3,790,471 | 2/1974 | Argauer et al. . |
| 3,852,189 | 12/1974 | Chen et al. . |
| 3,884,835 | 5/1975 | Vaughn . |
| 3,894,103 | 7/1975 | Chang et al. . |
| 3,894,938 | 7/1975 | Gorring et al. . |
| 3,941,871 | 3/1976 | Dwyer et al. . |
| 3,965,208 | 6/1976 | Butter et al. . |
| 3,983,055 | 9/1976 | Mitchell et al. . |
| 4,002,698 | 1/1977 | Kaeding . |
| 4,025,572 | 5/1977 | Lago . |
| 4,061,717 | 12/1977 | Kerr et al. . |
| 4,061,724 | 12/1977 | Grose et al. . |
| 4,064,070 | 12/1977 | Harrison . |
| 4,073,865 | 2/1978 | Flanigen et al. . |
| 4,088,605 | 5/1978 | Rollman . |
| 4,091,007 | 5/1978 | Dwyer et al. . |
| 4,100,215 | 7/1978 | Chen . |
| 4,104,294 | 8/1978 | Grose et al. . |
| 4,127,616 | 11/1978 | Rodewald . |
| 4,139,600 | 2/1979 | Rollman et al. . |
| 4,148,713 | 2/1979 | Rollman . |
| 4,153,540 | 5/1979 | Gorring et al. . |
| 4,170,544 | 10/1979 | Miller . |
| 4,175,114 | 11/1979 | Plank et al. . |
| 4,176,050 | 11/1979 | Chen et al. . |
| 4,208,305 | 6/1980 | Kouwenhoven et al. . |
| 4,242,233 | 12/1980 | Ball et al. . |
| 4,257,885 | 3/1981 | Grose et al. . |
| 4,270,017 | 5/1981 | Young . |
| 4,283,306 | 8/1981 | Herkes . |
| 4,299,808 | 11/1981 | Klotz . |
| 4,325,929 | 4/1982 | Young . |
| 4,330,396 | 5/1982 | Miller . |
| 4,344,927 | 8/1982 | Young . |
| 4,377,468 | 3/1983 | La Pierre et al. . |

FOREIGN PATENT DOCUMENTS

| | | | |
|---|---|---|---|
| 2831611 | 2/1980 | Fed. Rep. of Germany | 423/326 |
| 2024790 | 1/1980 | United Kingdom | 423/326 |

OTHER PUBLICATIONS

SN 32,001 to Herkes, filed Apr. 20, 1979.
"Silicalite, A New Hydrophobic Crystalline Silica Molecular Sieve", by Flanigen et al., Nature, vol. 271, Feb. 9, 1978, pp. 512 to 516.
"Silicalite-2, A Silica Analogue of the Aluminosilicate Zeolite ZSM-11", by Bibby et al., Nature, vol. 280, Feb. 26, 1981, pp. 782 and 783.
"Reactions on ZSM-5-Type Zeolite Catalysts", by Anderson et al., Journal of Catalysis, vol. 58, pp. 114 to 130, (1979).
"Chemical and Physical Properties of the ZSM-5 Substitutional Series", by Olson et al., Journal of Catalysis, vol. 61, pp. 390 to 396, (1980).
"Zoned Aluminum Distribution in Synthetic Zeolite ZSM-5", by Ballmoos et al., Nature, vol. 289, Feb. 26, 1981, pp. 782 to 783.
"When is a Zeolite Not a Zeolite", by Reeves, Nature, vol. 296, Apr. 8, 1982, pp. 491 to 492.
"Resolving Crystallographically Distinct Tetrahedral Sites in Silicalite and ZSM-5 by Solid State NMR", by Fybe et al, Nature, vol. 296, pp. 530 to 533.
"Research Article Triggers Dispute on Zeolite", by Budiansky, Nature, vol. 300, Nov. 25, 1982, p. 309.

Primary Examiner—Carl F. Dees
Attorney, Agent, or Firm—Robert J. Baran; Cleveland R. Williams; Dean Sandford

[57] ABSTRACT

Para-xylene is selectively prepared by reacting toluene and a methylating agent in the presence of a phosphorus modified catalyst comprising a silica polymorph intermixed with an inorganic refractory oxide, said catalyst having an alkali content of less than about 1.3 milliequivalents per gram as available alkali.

103 Claims, No Drawings

4,518,703

CRYSTALLINE SILICA CATALYSTS

RELATED APPLICATIONS

This application is a divisional of application Ser. No. 157,211, filed June 9, 1980, now U.S. Pat. No. 4,433,187 which is a divisional of application Ser. No. 12,868, filed Feb. 16, 1979, now U.S. Pat. No. 4,270,017.

BACKGROUND OF THE INVENTION

1. Field of the Invention

The present invention resides in a process for preparing aromatic alkylating catalysts and a process for using the same.

The synthesis of alkylated aromatic hydrocarbons by reacting a methylating agent with toluene is not a new concept. Processes are available for producing various mixture of hydrocarbons, such as, xylene isomers, polyalkylbenzenes, etc. The relative amount or extent to which one or more of the above-described products is obtained is determined and/or controlled by the type catalyst, proportions of reactants, and reactor conditions. Catalysts which have been used in the past to prepare xylenes, benzenes, etc. are those selected from acidic cogels, acid-promoted kieselguhr, and various crystalline zeolite aluminosilicates.

Zeolites are described as a three-dimensional network of structural units consisting of silicon-centered $SiO_4$ and aluminum centered $AlO_4$ of a tetrahedral configuration, the tetrahedra being interconnected by a mutual sharing of oxygen atoms, the structural arrangement of which forms cavities or cells forming crystalline channels or pore openings having a uniform diameter characteristic of each variety or type of crystalline zeolite.

Silica polymorphs, such as silicalite, which are a major component in our aromatic alkylating catalysts, have a novel topological type of crystalline structure composed of silicate tetrahedra connected in a framework to form a three-dimensional system of intersecting channels defined by 10-ring members sufficiently wide enough to absorb molecules up to 6 Å diameter. Silicalite is hydrophobic and organophilic, and selectively adsorbs organic molecules over water.

The conversion of an aromatic, for example, toluene, to a xylene, such as para-xylene is normally a tedious and time-consuming procedure, many times involving a series of steps. Additionally, catalysts which possess acceptable activity generally tend to give a wide spectrum of products, for example, alkylated aromatics and hydrocarbons having a broad distribution of carbon atoms. This not only complicates the separation and recovery of the desired product, but results in reduced yield of said desired product and erosion of reactants in the production of undesired by-products. The catalysts and process herein are particularly suited to the selective formation of para-xylene from toluene and a methylating agent.

2. Description of the Prior Art

The reaction of toluene with a methylating agent in the presence of a catalyst to produce alkylated aromatics is appreciated and disclosed by the prior art. However, most known processes produce an undesirably large mixture of alkylated aromatics in addition to the desired product.

For example, U.S. Pat. No. 4,002,698 teaches a process for methylating toluene to selectively produce paraxylene by contacting toluene with a methylating agent under methylation conditions in the presence of a crystalline alumino-silicate zeolite catalyst.

Another process for alkylating aromatic hydrocarbons is set forth in U.S. Pat. No. 4,025,572; particularly, the reference discloses a process for the conversion of alcohols or ethers to olefinic and aromatic hydrocarbons in the presence of a crystalline aluminosilicate zeolite. This process is described as suitable for simultaneously producing olefinic hydrocarbons and mononuclear aromatics with high selectivity for para-xylene formation.

U.S. Pat. No. 4,061,724 relates to a crystalline silica composition which is described as selective in adsorbing organic materials from water in either the liquid phase or vapor phase. The crystalline silica is described as suitable for removing organic compounds from waste water.

SUMMARY OF THE INVENTION

The present invention resides in a process for preparing an aromatic alkylating catalyst and a process for using the same to alkylate aromatics, which comprises contacting a silica polymorph consisting of crystalline silica with an acid or an ammonium salt solution; mulling the silica polymorph with an inorganic refractory oxide gel or sol; calcining the silica polymorph and inorganic refractory oxide for about 2 hours at about 500° C.; contacting the calcined silica polymorph and inorganic refractory oxide with a phosphorus compound; and calcining the resultant catalyst for about 2 hours at about 500° C. to form a catalyst having an alkali content of less than about 1.3 milliequivalents per gram as available alkali.

Para-xylene is selectively prepared by contacting toluene with a methylating agent under methylation conditions in the presence of a catalyst comprising a silica-polymorph in combination with an inorganic refractory oxide, said catalyst having a silica polymorph to inorganic refractory oxide weight ratio at from about 10:1 to about 1:10 and a bulk density of from about 0.5 gm cm$^{-3}$ to about 2.5 gm cm$^{-3}$.

DESCRIPTION OF THE INVENTION

A catalyst and catalytic process are provided for selectively preparing para-xylene from toluene and a methylating agent. The catalyst is prepared by sequentially extracting alkali from a silica polymorph, forming an aggregate bonded with an inorganic refractory oxide, adding a phosphorus compound and calcining the resultant catalyst.

The preferred silica polymorph herein has a topologic type of tetrahedral framework, which contains a large fraction of five-membered rings of silica-oxygen tetrahedra. The frame-work comprises a three-dimensional system of intersecting channels which are defined as ten rings of oxygen atoms extending in three directions. Precursor-organic quaternary ammonium ions which occupy the intersecting channels, are removed by heating to yield the desired silica polymorph. The resulting void volume occupies approximately 33% of the crystal structure, and the three-dimensional channel is wide enough to absorb organic molecules having up to about 6 Å in diameter. The silica polymorphs, herein, degrade to a glass above about 1,300° C.

The silica polymorphs are uniquely stable, active solids which are suitable for use as catalyst components or catalysts for hydrocarbon reactions, such as cracking, isomerization, polymerization, reforming, and alkylation.

The source of catalytic activity, of the catalysts herein, is the acidity which originates with the isolated silanol groups located in the micropores of the crystalline solid. The acidity associated with these isolated silanol groups contrasts with the acidity of conventional aluminosilicate catalysts prepared from cogels or zeolites. For example, the active sites of the aluminosilicates are due to negative charges induced on aluminum atoms by the silicate matrix. The acid sites, provided by the aluminum atoms, exceed the strength of 72% sulfuric acid; while the acid sites originating from isolated silanol groups consistently are weaker than 72% sulfuric acid. This moderate strength, of the silica polymorphs herein, catalyzes hydrocarbon conversion while minimizing undesirable side reactions such as coking and light hydrocarbon production.

Preparation of the microporous, crystalline, silica catalysts herein include forming a crystalline silica by hydrothermally digesting a mixture of a strongly alkaline amine and amorphous silica. Next, the alkali and amine are removed by extracting with solutions of acids or ammonium salts and oxidizing or thermally decomposing the ammoniacal cations. The crystalline silica is then combined with other catalytic components or promoters, for example, alumina, silica, or clay binders and hydrocarbon or hydrogen activators, such as chromium, copper, nickel, and platinum.

The sequence of adding the caytic components can vary without detrimental effect to the final catalytic activity. For example, the crystalline silica powder may be extracted with an acid or ammonium salt solution, washed, calcined, bonded into aggregates, contacted with a phosphorus compound and activated. Alternatively, the crystalline silica may initially be bonded into aggregates, calcined, extracted with an acid or ammonium salt solution, contacted with a phosphorus compound, and then activated. Normally, the catalysts thus produced will have an alkali content of less than about 1.3 milliequivalents per gram as available alkali, and a bulk density of from about 0.5 gm cm$^{-3}$ to about 2.5 gm cm$^{-3}$, especially from about 0.5 gm cm$^{-3}$ to about 1.5 gm cm$^{-3}$.

The silicas produced in this invention are analogous to highly siliceous alkali silicates which form as insoluble compounds during extended hydrothermal digestion. The amine, incorporated as a cation during crystallization, becomes a source of micropores when eliminated by combustion or extraction. The surfaces of these micropores are relatively free of hydroxyl groups. The isolated hydroxyl groups which are present provide the moderate acidic strength of the catalyst. It should be noted, that the presence of a binder, such as alumina, does not significantly alter the characteristics of the catalysts herein.

In a preferred mode, the silica polymorph, herein is prepared by the hydrothermal crystallization of a reaction mixture comprising a silica source, water and a strongly alkaline amine such as ethylene diamine, or a quaternary ammonium hydroxide, for example, tetrapropylammonium hydroxide, etc. at a temperature of from about 100° C. to about 200° C. Suitable silica sources include sodium silicate, colloidal silica, silica hydrosol, silica gel, silicic acid and the like. Preparation of the preferred silica polymorph, herein, is described in greater detail in U.S. Pat. No. 4,061,724, the disclosure of which is incorporated herein by reference. The preferred silica polymorph is manufactured and marketed commercially under the tradename of Silicalite by the Union Carbide Corporation, Tarrytown, N.Y.

Other silica polymorphs suitable for use herein include, in addition to Silicalite, UCS-3, or UCS-4 and mixtures thereof. UCS-3 and UCS-4 are names given to silica polymorphs prepared herein. Methods of preparing the crystalline silica designated as UCS-3 and UCS-4 and x-ray diffraction patterns thereof, are disclosed in Examples VII and VIII. These and other suitable silica polymorphs are described in greater detail in U.S. Pat. No. 3,941,871 and U.S. Pat. No. 4,073,865, the disclosures of which are incorporated herein by reference.

The catalyst is prepared by initially extracting the silica polymorph with an acid at a pH of from about 0 to about 5, preferably from about 1 to about 4, for a time period of from about 10 minutes to about 10 hours, especially from about 15 minutes to about 5 hours. The extraction solution contains components selected from the group consisting essentially of nitric acid, hydrochloric acid, sulfuric acid, acetic acid, or ammonium salts such as ammonium nitrate, ammonium bisulfate and mixtures thereof. The resultant silica polymorph is collected by filtration, washed and dried.

Next, the silica polymorph is mixed with an inorganic refractory oxide in the form of a clay, hydrogel or sol such as peptized boehmite alumina or colloidal silica. The inorganic refractory oxides herein are preferably selected from the group consisting of bentonite clay, boehmite alumina, silica hydrosol or colloidal silica and mixtures thereof. Other inorganic refractory oxides include alumina, silica, magnesia, beryllia or zirconia and mixtures thereof. Sufficient water is present to form a plastic paste. The paste is spread in a thin layer, dried, granulated to about 10/30 mesh and calcined at about 450° C. to about 800° C. for about 10 minutes to about 10 hours. Undesirable components are removed from the calcined aggregate by extraction with the above-described acids and ammonium salts.

Normally, the silica polymorph and inorganic refractory oxide are in a weight ratio range of from about 1:10 to about 10:1, especially from about 1:4 to about 4:1.

It is to be noted, that the extraction step with acid or ammonium salt can be carried out in one step, or, alternatively, can be carried out in two or even three separate steps either before or after mixing the silica polymorph with the inorganic refractory oxide but before addition of the phosphorus compound thereto.

The bonded, extracted silica polymorph-inorganic refractory oxide granules are then contacted with a phosphorus containing solution for about 5 minutes to about 2 hours at a temperature of from about 10° C. to about 60° C.; preferably from about 30 minutes to about 1 hour. The resultant catalyst is activated by calcination for about 15 minutes to about 4 hours at about 450° C. to about 800° C.

The amount of phosphorus incorporated with the catalyst should be from about 2 to about 35 percent by weight, especially from about 5 to about 25 percent by weight. Representative phosphorus compounds include derivatives of groups represented by the formulae $PX_3$, $RPX_2$, $R_2PX$, $R_3P$, $X_3PO$, $(XO_3)PO$, $(XO)_3P$, $R_3P=O$, $R_3P=S$, $RPO_2$, $PPS_2$, $RP(O)(OX)_2$, $RP(S)(SX)_3$, $R_2P(O)OX$, $R_2P(S)SX$, $RP(OX)_2$, $RP(SX)_2$, $ROP(OX)_2$, $RSP(SX)_2$, $(RS)_2PSP(SR)_2$ and $(RO)_2POP(OR)_2$ wherein R is alkyl or aryl and X is hydrogen, alkyl, aryl or halide. These compounds include primary, secondary or tertiary phosphines; tertiary phosphine oxides; tertiary phosphine sulfides; primary and secondary phosphonic acids and their corresponding sulfur derivatives; esters of phosphonic acids; the dialkyl alkyl phosphonates; alkyl dialkyl phosphonates; phosphinous acids, primary, secondary and tertiary phosphites and esters thereof; alkyl dialkylphosphinites, dialkyl alkylphosphonites their esters and sulfur derivatives.

Other suitable phosphorus-containing compounds include the phosphorus halides such as phosphorus trichloride, phosphorus tribromide, phosphorus triiocide, alkyl phosphorodichlorides, dialkyl phosphorochlorides and dialkyl phosphonochloridites. Preferred phosphorus-containing compounds include phosphoric acid, phosphorus acid, and phosphate esters such as trimethylphosphate, ethylphosphite, or monophenylphosphate, etc. and mixtures thereof.

It is to be noted, that the catalysts herein are highly selective to the formation of para-xylene when contacted under methylating conditions with toluene and a methylating agent. Aromatic-alkylating catalysts synthesized according to the procedure herein have an average pore radius of from about 30 Å to about 200 Å, preferably from about 50 Å to about 150 Å; a surface area of from $100M^2/gm$ to about $500M^2/gm$, especially from about $150M^2/gm$ to about $350M^2/gm$; and a pore volume of from about 0.33 cc/gm to about 1.0 cc/gm, preferably from about 0.5 cc/gm to about 0.8 cc/gm.

In a preferred mode, the phosphorus-modified catalyst herein is prepared from a silica polymorph comprising silicalite in combination with an inorganic refractory oxide. Silicalite has a refractive index of 1.39 and a density of 1.76. Other silica polymorphs have a refractive index range of from about 1.32 to about 1.45, and a density range of from about 1.65 to about 1.80. The catalyst is characterized by a silica polymorph to inorganic refractory oxide weight ratio of from about 1:10 to about 10:1, especially from about 1:4 to about 4:1. The final catalyst pore radius, surface area, pore volume and phosphorus content are as defined above.

Methylation of toluene can effectively be carried out by contacting toluene and a methylating agent with the above-described catalyst. The reaction is carried out at a temperature of from about 400° C. to about 600° C., preferably from about 450° C. to about 550° C., and at a pressure from about 5 psia to about 250 psia, especially from about 15 psia to about 100 psia. The molar ratio of toluene to methylating agent is generally from about 6:1 to about 1:2, especially from about 3:1 to about 1:1. Suitable methylating agents include methanol, methylchloride, methylbromide, dimethyl ether, methylcarbonate, dimethylsulfide, etc. The methylation reaction is accomplished using a weight hourly space velocity (WHSV) of from about 1 to about 10, especially from about 2 to about 6. Para-xylene is selectively produced in the reaction, however, it should be noted that some ortho-xylene and small amounts of meta-xylene may additionally be produced. Conventional methods can be used to separate the xylene isomers or the undesirable isomers may be converted to para-xylene in an isomerization process. The methylation reaction herein can be carried out as a continuous, semi-continuous or batch type operation, using a fixed or moving type catalyst system utilizing conventional apparatus and techniques.

DESCRIPTION OF PREFERRED EMBODIMENTS

The following Examples serve to further illustrate and instruct one skilled in the art the best mode of how to practice this invention and are not intended to be construed as limiting thereof.

EXAMPLE I

An aromatic alkylating catalyst was prepared by digesting silicalite powder in an acidic 10% solution of ammonium nitrate ($NH_4NO_3$) at a pH of 2.6 for about 30 minutes using 5 ml of solution per gram of silicate powder. The solids were collected by filtration, washed, and the digestion process was repeated for a total of two ion exchanges. The residual alkali content, on a calcined basis, was 0.027% sodium and 0.002% potassium. Analysis indicated that the silicalite had a surface area of $460M^2/gm$. The exchanged silicalite powder (100 grams) was then mulled with 51 grams of "Catapal S", a pure boehmite alumina powder. Sufficient ½ normal nitric acid was added to peptize the alumina powder, forming a paste like mixture with the silicalite. The paste was spread in a thin layer, dried, granulated to 10/30 mesh, and calcined 2 hours at 1000° F. (537° C.).

The calcined granules were immersed in dilute phosphoric acid for 30 minutes, drained, dried at 230° F. (108.9° C.), and calcined 2 hours at 900° F. (477.4° C.). The resultant catalyst had a final phosphorus content of 14.3% ($P_2O_5$) and a surface area of $283M^2/gm$.

EXAMPLE II

A catalyst, suitable for alkylating aromatics, was prepared by digesting silicalite powder in an acidic 10% solution of ammonium nitrite ($NH_4NO_3$) at a pH of 2.6 for about 30 minutes using 5 ml of acid per gram of silicalite powder. The solids were collected by filtration, washed, and the digestion process was repeated for a total of two extractions. The residual alkali content, on a calcined basis, was 0.027% sodium and 0.002% potassium. Analysis indicated that the silicalite had a surface area of $460M^2/gm$. The exchanged silicalite powder (100 grams) was, next, mulled with 51 grams of "Catapal S", a pure boehmite alumina powder. Sufficient ½ normal nitric acid was added to the silicalite and alumina powder to form a soft paste. The paste was spread in a thin layer, dried, granulated to 10/30 mesh, and calcined 2 hours at 1000° F. (232.4° C.). The calcined granules were digested for 16 hours at 160° F. (70.4° C.) in 3 normal ammonium bisulfate solutions ($NH_4HSO_4$) using 1.4 ml of ammonium bisulfate per gram of calcined granules.

Next, the calcined granules were washed three times with 1 normal acetic acid (HOAc) and with distilled water to eliminate the sulfate. The washed granules were dried, immersed in dilute phosphoric acid ($H_3PO_4$) for 30 minutes, drained, dried at 230° F. (108.9° C.), and calcined 2 hours at 900° F. (482° C.). The resultant catalyst had a final phosphorus content of 12.9% ($P_2O_5$) and a surface area of $303M^2/gm$.

It is to be noted that the acid-digestion of the granules in this Example prior to phosphorus impregnation substantially increased the selectivity for forming para-xylene in a methylation reaction. However, acid-digestion prior to phosphorus impregnation is not absolutely essential to the selective formation of para-xylene (see Example I), although, higher selective values are reported when acid-digestion occurs in the last step of the process prior to phosphorus impregnation.

EXAMPLE III

The catalyst of Example I was evaluated for alkylation of aromatics and selectivity for para-xylene production by feeding a 2:1 molar solution of toluene and methanol into a reactor containing said catalyst at 1000° F. (537° C.). The feed rate was 4.0 weight hourly space velocity for 3 hours. Toluene conversion was 37 mole percent with 80% selectivity to xylene formation. The xylene fraction had the following distribution of isomers:

TABLE 1

| Compound | Wt. Percent |
| --- | --- |
| Para-xylene | 28 |
| Meta-xylene | 49 |
| Ortho-xylene | 23 |

EXAMPLE IV

The procedure of Example III was followed with the following exceptions: toluene and methanol were introduced into a reactor containing the catalyst of Example I, at a weight hourly space velocity of 10 for 4.5 hours. The reaction temperature was maintained at 1100° F. (593° C.) during the reaction time period. Toluene conversion was 34 mole percent with 88% selectivity to xylene formation. The xylene fraction had the following distribution of isomers.

TABLE 2

| Compound | Wt. Percent |
| --- | --- |
| Para-xylene | 40 |
| Meta-xylene | 41 |
| Ortho-xylene | 19 |

The results in Examples III and IV above are to be compared with Examples V and VI to note the increase in selectivity to para-xylene formation due to acid treating the catalyst matrix prior to phosphorus impregnation.

EXAMPLE V

The catalyst of Example II was evaluated for aromatic alkylation and selectivity for para-xylene production by introducing a 2:1 molar solution of toluene and methanol into a reactor, containing said catalyst at 1000° F. (537° C.). The feed rate was 4.0 weight hourly space velocity for 3 hours. Analysis indicated that toluene conversion was 28 mole percent with 87% selectivity for xylene formation. The xylene fraction had the following distribution of isomers.

TABLE 3

| Compound | Wt. Percent |
| --- | --- |
| Para-xylene | 53 |
| Meta-xylene | 31 |
| Ortho-xylene | 16 |

EXAMPLE VI

The procedure of Example V was followed except for the following variations: toluene and methanol were introduced into a reactor containing the catalyst of Example II, at a weight hourly space velocity of 10 for 4.5 hours and a temperature of about 1100° F. (593° C.). Toluene conversion was 22 mole percent with 95% selectivity to xylene formation. The xylene fraction had the following distribution of isomers.

TABLE 4

| Compound | Wt. Percent |
| --- | --- |
| Para-xylene | 74 |
| Meta-xylene | 17 |
| Ortho-xylene | 9 |

EXAMPLE VII

A crystalline silica suitable for use in preparing an aromatic alkylating catalyst was prepared from the following solutions:
1. Base solution, 6N NaOH
2. Silicate solution composed of:
    2870 gm of commercial sodium silicate containing 8.9% $Na_2O$ and 28.7% $SiO_2$,
    1670 ml of water and 9 gm of Dow-Fax 2A1 wetting agent[A]
3. Acid solution composed of:
    147 ml of 36N $H_2SO_4$
    1730 ml of water
    130 gm of NaCl
4. Organic solution composed of:
    207 gm of tripropylamine
    172 gm of 1-bromopropane
    329 gm of methylethyl ketone A hydrogel was formed by combining 900 ml of the above-described acid solution with 1900 ml of the silicate solution through a mixing tee. Next, 15 ml of 6N sodium hydroxide (NaOH) was mixed with the hydrogel. A 343 gm portion of the organic solution was mixed into the hydrogel. The mixture was allowed to gel and a 3400 ml portion of the hydrogel mixture was transferred to a heated, stirred vessel pressurized with 100 psig of nitrogen. High shear mixing was provided by two revolving paddles inside the reaction vessel. The digestion conditions and product characteristics are disclosed in Table 5 below.

TABLE 5

| Crystalline Silica | UCS-3[B] |
| --- | --- |
| Digestion Conditions | |
| Temperature, °F. | 330 |
| Total Hours at Temp. | 60 |
| Stirrer Speed, RPM | 600 |
| Hours Stirred | 60 |
| Product Qualities | |
| Nitrogen Content, wt. % N[C] | 0.26 |
| Sodium Content, wt. % $Na_2O$[D] | 1.72 |
| Surface area $M^2/g$[D] | 176 |

[A]Dow-Fax 2Al-45%, solution of disodium 4-dodecylated oxydibenzene-sulfonate
[B]UCS-3 - Name given to the crystalline silica of Example VII
[C]The samples were dried at 230° F. prior to determining the nitrogen content.
[D]The samples were calcined at 800° F. prior to determining the sodium content and surface area. The surface area was calculated from nitrogen adsorption at 0.02 relative pressure.

The X-ray powder diffraction pattern of the above crystalline silica has as its strongest lines (i.e. interplanar spacing) those disclosed in Table 6 below.

TABLE 6

| d-Å | Relative Intensity |
| --- | --- |
| 18.8 | VS[1] |
| 3.81 | VS |
| 3.41 | S[2] |
| 3.31 | VS |

[1]VS = very strong
[2]S = strong

The procedure of Example II is followed to prepare an aromatic alkylating catalyst with the following exception: the crystalline silica produced above is substituted for the silicate powder. The catalyst thus prepared is particularly suited for selectively preparing para-xylene from toluene and a methylating agent.

EXAMPLE VIII

A crystalline silica suitable for use as a catalyst component in the preparation of an aromatic alkylating catalyst was prepared according to the procedure of Example VII with the following exceptions: The digestion conditions and product characteristics are set forth in Table 7 below:

TABLE 7

| Crystalline Silicas | UCS-4[A] |
|---|---|
| Digestion Conditions | |
| Temperature, °F. | 300 |
| Total Hours at Temp. | 60 |
| Stirrer Speed, RPM | 600 |
| Hours Stirred | 4 |
| Hours Unstirred | 56 |
| Product Qualities | |
| Nitrogen Content, Wt. % N[B] | 0.09 |
| Sodium Content, Wt. % $Na_2O$[C] | 0.91 |
| Surface area, $M^2$/gm[C] | 158 |

[A]UCS-4 - Name given to the crystalline silca of Example VIII.
[B]The samples were dried at 230° F. prior to determining the nitrogen content.
[C]The samples were calcined at 800° F. prior to determining the sodium content and surface area. The surface area was calculated from nitrogen adsorption at 0.02 relative pressure.

The X-ray powder diffraction pattern of the above crystalline silica has as its strongest lines, i.e. interplanar spacing, those disclosed in Table 8 below.

TABLE 8

| d-Å | Relative Intensity |
|---|---|
| 4.07 | VS[1] |
| 4.02 | S[2] |
| 3.83 | VS |
| 3.34 | VS |

[1]VS = Very strong
[2]S = strong

An aromatic alkylating catalyst can be prepared by substituting the crystalline silica above for the silicalite powder in Example II. The prepared catalyst is highly selective in preparing para-xylene from toluene and a methylating agent.

EXAMPLE IX

An aromatic alkylating catalyst was prepared using the method of Example II with the following exception: the crystalline silica of Example VII was substituted for silicalite and the catalyst had a phosphorus content of 21.5% phosphorus as $P_2O_5$.

The catayst thus prepared was evaluated for alkylation of toluene with methanol and for para-xylene selectivity by feeding a 2:1 molar solution of toluene and methanol into a reactor containing said catalyst at 1100° F. (593° C.). The feed rate was 10 weight hourly space velocity for 4.5 hours. Toluene conversion was 22 mole percent with 100% selectivity to xylene formation. The xylene fraction had the following distribution of isomers:

TABLE 9

| Compound | Wt. Percent |
|---|---|
| Para-xylene | 90 |
| Meta-xylene | 6 |

TABLE 9-continued

| Compound | Wt. Percent |
|---|---|
| Ortho-xylene | 4 |

EXAMPLE X

The procedure of Example II was followed to prepare an aromatic alkylating catalyst with the following exceptions: the crystalline silica of Example VIII was substituted for silicalite and the catalyst had a phosphorus content of 22.7% as $P_2O_5$.

The catalyst was evaluated for selectivity to paraxylene formation by feeding a 2:1 molar solution of toluene and methanol into a reactor, containing the above catalyst, at 1100° F. (593° C.). The feed rate was 10 weight hourly space velocity for 4.5 hours. The converted toluene and methanol had the following distribution of isomers:

TABLE 10

| Compound | Wt. Percent |
|---|---|
| Para-xylene | 95 |
| Meta-xylene | 3 |
| Ortho-xylene | 2 |

Obviously, many modifications and variations of the invention, as hereinabove set forth, can be made without departing from the spirit and scope thereof, and therefore only such limitations should be imposed as are indicated in the appended claims.

I claim:

1. A catalyst comprising a hydrogen activator and a crystalline silica polymorph.

2. A catalyst as defined in claim 1 where the hydrogen activator comprises chromium.

3. A catalyst as defined in claim 1 where the hydrogen activator comprises copper.

4. A catalyst as defined in claim 1 where the hydrogen activator comprises nickel.

5. A catalyst as defined in claim 1 where the hydrogen activator comprises platinum.

6. A catalyst as defined in claim 1 where the crystalline silica polymorph comprises silicalite.

7. A catalyst as defined in claim 4 where the crystalline silica polymorph has a specific gravity at 25° C. of 1.70±0.05 g/cc and a mean refractive index of 1.39±0.01 after calcination at 600° C. in air for 1 hour.

8. A catalyst as defined in claim 2 where the crystalline silica polymorph has a pore volume of 0.18 cc/gram.

9. A catalyst as defined in claim 2 where the crystalline silica polymorph has as the six strongest d-values of its X-ray diffraction pattern d=11.1±0.2, d=10.0±0.2, d=3.85±0.07, d=3.82±0.07, d=3.76±0.05 and d=3.72±0.05.

10. A catalyst as defined in claim 5 where the crystalline silica polymorph is capable of separating P-xylene from O-xylene.

11. A catalyst as defined in claim 4 where the crystalline silica polymorph is capable of separating P-xylene from ethylbenzene.

12. A catalyst as defined in claim 5 where the crystalline silica polymorph is capable of separating P-xylene from m-xylene.

13. A catalyst comprising a hydrogen activator comprising a member selected from the group consisting of chromium, copper, nickel and platinum and further comprising a crystalline silica polymorph.

14. A catalyst as defined in claim 13 where said crystalline silica polymorph has a specific gravity at 25° C. of 170±0.05 g/cc and a mean refractive index of 1.39±0.01.

15. A catalyst comprising a hydrogen activator, an inorganic refractory oxide and a crystalline silica polymorph.

16. A catalyst as defined in claim 15 where the hydrogen activator comprises chromium.

17. A catalyst as defined in claim 15 where the hydrogen activator comprises copper.

18. A catalyst as defined in claim 15 where the hydrogen activator comprises nickel.

19. A catalyst as defined in claim 15 where the hydrogen activator comprises platinum.

20. A catalyst as defined in claim 15 where said silica polymorph has an X-ray diffraction pattern with the following six strongest d-values of its X-ray diffraction pattern: $d=11.1\pm0.2$, $d=10.0\pm0.2$, $d=3.85\pm0.07$, $d=3.76\pm0.05$ and $d=3.72\pm0.05$.

21. A catalyst as defined in claim 15 where said inorganic refractory oxide comprises a member selected from the group consisting of alumina, silica, magnesia, beryllia, and zirconia.

22. A catalyst comprising a hydrogen activator, an inorganic refractory oxide, and silicalite.

23. A catalyst as defined in claim 22 where said hydrogen activator comprises nickel and said inorganic refractory oxide comprises a member selected from the group consisting of alumina, silica, magnesia, beryllia and zirconia.

24. A catalyst as defined in claim 22 where said hydrogen activator comprises platinum and said inorganic refractory oxide comprises a member selected from the group consisting of alumina, silica, magnesia, beryllia and zirconia.

25. A catalyst as defined in claim 22 where said hydrogen activator comprises copper and said inorganic refractory oxide comprises a member selected from the group consisting of alumina, silica, magnesia, beryllia and zirconia.

26. A catalyst as defined in claim 22 where said hydrogen activator comprises chromium and said inorganic refractory oxide comprises a member selected from the group consisting of alumina, silica, magnesia, beryllia and zirconia.

27. A catalyst comprising a hydrogen activator comprising a member selected from the group consisting of chromium, copper, nickel and platinum, an inorganic refractory oxide and a crystalline silica polymorph.

28. A catalyst as defined in claim 1 where said crystalline silica polymorph is capable of separating P-xylene from ethylbenzene.

29. A catalyst comprising a hydrogen activator comprising a member selected from the group consisting of chromium, copper, nickel and platinum, a crystalline silica polymorph having a pore volume of about 0.18 cc/gram, and an inorganic refractory oxide selected from the group consisting of alumina, silica, magnesia, beryllia and zirconia.

30. A catalyst comprising a hydrogen activator selected from the group consisting of chromium, nickel and platinum and a crystalline silica polymorph having as the six strongest d-values of its X-ray diffraction pattern: $d=11.1\pm0.2$, $d=10.0\pm0.2$, $d=3.85\pm0.07$, $d=3.82\pm0.07$, $d=3.76\pm0.05$ and $d=3.72\pm0.05$.

31. A catalyst comprising a hydrogen activator selected from the group consisting of chromium, nickel and platinum, an inorganic refractory oxide and a crystalline silica polymorph having as the six strongest d-values of its X-ray diffraction pattern: $d=11.1\pm0.2$, $d=10.0\pm0.2$, $d=3.85\pm0.07$, $d=3.82\pm0.07$, $d=3.76\pm0.05$ and $d=3.72\pm0.05$.

32. A catalyst as defined in claim 31 where said refractory oxide is selected from the group consisting of alumina, silica, beryllia and zirconia.

33. A catalyst comprising a hydrogen activator selected from the group consisting of chromium, nickel and platinum, an inorganic refractory oxide comprising a member selected from the group consisting of alumina, silica, magnesia and zirconia, and a crystalline silica polymorph capable of separating P-xylene from O-xylene.

34. A catalyst comprising a hydrogen activator comprising nickel, an inorganic refractory oxide comprising a member selected from the group consisting of alumina, silica, magnesia and zirconia, and a crystalline silica polymorph capable of separating P-xylene from ethylbenzene.

35. A catalyst comprising a hydrogen activator comprising platinum, an inorganic refractory oxide comprising a member selected from the group consisting of alumina, silica, magnesia and zirconia, and a crystalline silica polymorph capable of separating P-xylene from m-xylene.

36. A catalyst comprising a hydrogen activator comprising chromium, an inorganic refractory oxide comprising a member selected from the group consisting of alumina, silica, magnesia and zirconia, and a crystalline silica polymorph capable of separating P-xylene from O-xylene, m-xylene and ethylbenzene.

37. A catalyst comprising a hydrogen activator selected from the group consisting of chromium, nickel and platinum, an inorganic refractory oxide selected from the group consisting of alumina and silica and mixtures thereof, and a crystalline silica polymorph having uniform pore dimensions of about 6 Å, a specific gravity at 25° C. of 1.70±0.05 g/cc, and a mean refractive index of 1.39±0.01 after calcination at 600° C. in air for 1 hour.

38. A catalyst consisting essentially of a hydrogen activator, an inorganic refractory oxide and a crystalline silica polymorph having as its X-ray diffraction pattern:

| d-Å | Relative Intensity | d-Å | Relative Intensity |
|---|---|---|---|
| 11.1 | 100 | 4.35 | 5 |
| 10.02 | 64 | 4.25 | 7 |
| 9.73 | 16 | 4.08 | 3 |
| 8.99 | 1 | 4.00 | 3 |
| 8.04 | 0.5 | 3.85 | 59 |
| 7.42 | 1 | 3.82 | 32 |
| 7.06 | 0.5 | 3.74 | 24 |
| 6.68 | 5 | 3.71 | 27 |
| 6.35 | 9 | 3.64 | 12 |
| 5.98 | 14 | 3.59 | 0.5 |
| 5.70 | 7 | 3.48 | 3 |
| 5.57 | 8 | 3.44 | 5 |
| 5.36 | 2 | 3.34 | 11 |
| 5.11 | 2 | 3.30 | 7 |
| 5.01 | 4 | 3.25 | 3 |
| 4.98 | 5 | 3.17 | 0.5 |
| 4.86 | 0.5 | 3.13 | 0.5 |
| 4.60 | 3 | 3.05 | 5 |
| 4.44 | 0.5 | 2.98 | 10 |

39. The catalyst defined in claim 38 where the hydrogen activator comprises chromium.

40. The catalyst defined in claim 38 where the hydrogen activator comprises copper.

41. The catalyst defined in claim 38 where the hydrogen activator comprises nickel.

42. The catalyst defined in claim 38 where the hydrogen activator comprises platinum.

43. The catalyst defined in claim 38 where the catalyst further comprises an inorganic refractory oxide selected from the group consisting of alumina, silica, magnesia, beryllia and zirconia and mixtures thereof.

44. The catalyst defined in claim 38 where the catalyst further comprises an inorganic refractory oxide selected from the group consisting of alumina and silica and mixtures thereof.

45. A catalyst comprising nickel, silicalite and alumina.

46. A catalyst comprising a crystalline silica polymorph and an inorganic refractory oxide.

47. A catalyst as defined in claim 46 where the inorganic refractory oxide is a member selected from the group consisting of alumina, silica, magnesia, beryllia, zirconia and bentonite clay and mixtures thereof.

48. A catalyst as defined in claim 46 where the crystalline silica polymorph is capable of adsorbing organic molecules up to 6 Å in diameter.

49. A catalyst as defined in claim 46 where the crystalline silica polymorph has a specific gravity at 25° C. within the range of from about 1.65 to about 1.80 g/cc and a mean refractive index within the range of from about 1.32 to about 1.45.

50. A catalyst as defined in claim 46 where the crystalline silica polymorph has as the four strongest d-values of its X-ray diffraction pattern d=18.8, d=3.81, d=3.41, and d=3.31.

51. A catalyst as defined in claim 46 where the crystalline silica polymorph has as the four strongest d-values of its X-ray diffraction pattern d=4.07, d=4.02, d=3.83 and d=3.34.

52. A catalyst comprising a crystalline silica polymorph having as the six strongest d-values of its X-ray diffraction pattern d=11.1±0.2, d=10.0±0.2, d=3.85±0.07, d=3.82±0.07, d=3.76±0.05 and d=3.72±0.05, in combination with an inorganic refractory oxide, said catalyst having a bulk density within the range of from about 0.5 gm cm$^{-3}$ to about 2.5 gm cm$^{-3}$.

53. A catalyst as defined in claim 52 wherein the inorganic refractory oxide is a member selected from the group consisting of alumina, silica, magnesia, beryllia and zirconia and mixtures thereof.

54. A catalyst comprising a microporous crystalline silica and an inorganic refractory oxide.

55. A catalyst as defined in claim 54 wherein the inorganic refractory oxide is a member selected from the group consisting of alumina, silica, magnesia, beryllia and bentonite clay and mixtures thereof.

56. A catalyst consisting essentially of a microporous crystalline silica and an inorganic refractory oxide.

57. A catalyst as defined in claim 56 wherein the inorganic refractory oxide is a member selected from the group consisting of alumina, silica, magnesia, beryllia, zirconia and bentonite clay and mixtures thereof.

58. A catalyst comprising a crystalline silica polymorph and an inorganic refractory oxide where the crystalline silica polymorph is capable of separating p-xylene from o-xylene.

59. A catalyst as defined in claim 58 wherein the inorganic refractory oxide is a member selected from the group consisting of alumina, silica, magnesia, zirconia and bentonite clay and mixtures thereof.

60. A catalyst comprising a crystalline silica polymorph and an inorganic refractory oxide where the crystalline silica polymorph and inorganic refractory oxide are in a weight ratio range of from about 1:10 to about 10:1 and said crystalline silica polymorph is capable of separating p-xylene from ethylbenzene.

61. A catalyst as defined in claim 60 wherein the inorganic refractory oxide is a member selected from the group consisting of alumina, silica, magnesia, beryllia, zirconia and bentonite clay and mixtures thereof.

62. A catalyst comprising a crystalline silica polymorph and an inorganic refractory oxide where the crystalline silica polymorph and inorganic refractory oxide are in a weight ratio range of from about 1:4 to about 4:1 and said crystalline silica polymorph is capable of separating p-xylene from m-xylene.

63. A catalyst as defined in claim 62 where the inorganic refractory oxide is a member selected from the group consisting of alumina, silica, magnesia, beryllia, zirconia and bentonite clay and mixtures thereof.

64. A catalyst comprising silicalite and an inorganic refractory oxide.

65. A catalyst as defined in claim 64 where the inorganic refractory oxide is a member selected from the group consisting of alumina, silica, magnesia, beryllia, zirconia and bentonite clay and mixtures thereof.

66. A catalyst comprising silicalite and an inorganic refractory oxide selected from the group consisting of alumina and silica and mixtures thereof.

67. A catalyst comprising silicalite and alumina.

68. A catalyst comprising silicalite and an inorganic refractory oxide selected from the group consisting of alumina, silica and magnesia and mixtures thereof wherein the silicalite and inorganic refractory oxide are in a weight ratio range of from about 1:10 to about 10:1.

69. A catalyst comprising a crystalline silica polymorph and an inorganic refractory oxide where the crystalline silica polymorph has a specific gravity at 25° C. of 1.70±0.05 g/cc and a mean refractive index of 1.39±0.01 after calcination of 600° C. in air for 1 hour, and wherein the crystalline silica polymorph and inorganic refractory oxide are in a weight ratio range of from about 1:10 to about 10:1.

70. A catalyst as defined in claim 69 where the inorganic refractory oxide is a member selected from the group consisting of alumina, silica, beryllia, zirconia and bentonite clay and mixtures thereof.

71. A catalyst as defined in claim 69 where the inorganic refractory oxide is alumina.

72. A catalyst consisting essentially of a crystalline silica polymorph and an inorganic refractory oxide where the crystalline silica polymorph has a specific gravity at 25° C. of 1.70±0.05 g/cc and a mean refractive index of 1.39±0.01 after calcination at 600° C. in air for 1 hour, and wherein the crystalline silica polymorph and inorganic refractory oxide are in a weight ratio range of from about 1:10 to about 10:1.

73. A catalyst as defined in claim 72 where the inorganic refractory oxide is a member selected from the group consisting of alumina, silica, beryllia, zirconia and bentonite clay and mixtures thereof.

74. A catalyst as defined in claim 72 where the inorganic refractory oxide is alumina.

75. A catalyst comprising a phosphorus compound and a crystalline silica polymorph.

76. A catalyst as defined in claim 75 wherein said catalyst further contains an inorganic refractory oxide.

77. A catalyst as defined in claim 75 wherein said catalyst further comprises alumina.

78. A catalyst as defined in claim 75 wherein said refractory oxide is selected from the group consisting of alumina, silica, magnesia, beryllia, zirconia, and bentonite clay.

79. A catalyst as defined in claim 75 wherein said silica polymorph is silicalite.

80. A catalyst as defined in claim 76 wherein said silica polymorph has a specific gravity at 25° C. of 1.70±0.05 g/cc and a mean refractive index of 1.39±0.01.

81. A catalyst as defined in claim 77 wherein said crystalline silica polymorph has as the six strongest d-values of its X-ray diffraction pattern d=11.1±0.2, d=10.0±0.2, d=3.85±0.07, d=3.82±0.07, d=3.76±0.05 and d=3.72±0.05.

82. A catalyst as defined in claim 78 wherein said crystalline silica polymorph has as the six strongest d-values of its X-ray diffraction pattern d=11.1±0.2, d=10.0±0.2, d=3.85±0.07, d=3.82±0.07, d=3.76±0.05 and d=3.72±0.05.

83. A catalyst as defined in claim 76 wherein said catalyst has a surface area from 100 $M^2$/gm to about 500 $M^2$/gm.

84. A catalyst as defined in claim 83 wherein said silica polymorph has a pore volume of 0.18 cc/gram.

85. A catalyst as defined in claim 76 wherein the crystalline silica polymorph and inorganic refractory oxide are in a weight ratio range of from about 1:10 to about 10:1.

86. A catalyst as defined in claim 85 wherein said silica polymorph is silicalite and said refractory oxide is selected from the group consisting of alumina, silica, zirconia, magnesia, beryllia, and bentonite clay.

87. A catalyst as defined in claim 85 wherein said crystalline silica polymorph has as the six strongest d-values of its X-ray diffraction pattern d=11.1±0.2, d=10.0±0.2, d=3.85±0.07, d=3.82±0.07, d=3.76±0.05 and d=3.72±0.05.

88. A catalyst as defined in claim 87 wherein said refractory oxide is alumina.

89. A catalyst as defined in claim 75 wherein said phosphorus compound is a phosphorus oxide.

90. A catalyst as defined in claim 76 wherein said phosphorus compound is a phosphorus oxide.

91. A catalyst as defined in claim 80 wherein said phosphorus compound is a phosphorus oxide.

92. A catalyst as defined in claim 81 wherein said phosphorus compound is a phosphorus oxide.

93. A catalyst as defined in claim 86 wherein said phosphorus compound is a phosphorus oxide.

94. A catalyst as defined in claim 88 wherein said phosphorus compound is a phosphorus oxide.

95. A catalyst comprising a microporous crystalline silica and a promoter containing a component selected from the group consisting of platinum, phosphorus, chromium, nickel, and copper.

96. A catalyst as defined in claim 95 wherein said catalyst further comprises an inorganic refractory oxide.

97. A catalyst as defined in claim 96 wherein said refractory oxide comprises alumina.

98. A catalyst as defined in claim 96 wherein said refractory oxide comprises silica.

99. A catalyst as defined in claim 95 wherein said crystalline silica has as the six strongest d-values of its X-ray diffraction pattern d=11.1±0.2, d=10.0±0.2, d=3.85±0.07, d=3.82±0.07, d=3.76±0.05 and d=3.72±0.05.

100. A catalyst as defined in claim 95 wherein said crystalline silica has as the four strongest d-values of its X-ray diffraction pattern d=18.8, d=3.81, d=3.41, and d=3.31.

101. A catalyst as defined in claim 95 wherein said crystalline silica has as the four strongest d-values of its X-ray diffraction pattern d=4.07, d=4.02, d=3.83, and d=3.34.

102. A catalyst as defined in claim 96 wherein said crystalline silica has as the six strongest d-values of its X-ray diffraction pattern d=11.1±0.2, d=10.0±0.2, d=3.85±0.07, d=3.82±0.07, d=3.76±0.05 and d=3.72±0.05.

103. A catalyst as defined in claim 97 wherein said crystalline silica has as the six strongest d-values of its X-ray diffraction pattern d=11.1±0.2, d=10.0±0.2, d=3.85±0.07, d=3.82±0.07, d=3.76±0.05 and d=3.72±0.05.

* * * * *

UNITED STATES PATENT AND TRADEMARK OFFICE
CERTIFICATE OF CORRECTION

PATENT NO. : 4,518,703

DATED : May 21, 1985

INVENTOR(S) : Dean A. Young

It is certified that error appears in the above—identified patent and that said Letters Patent is hereby corrected as shown below:

In Column 11, line 5, change "170$\pm$0.05" to -- 1.70$\pm$0.05 --.

Signed and Sealed this

Twenty-second Day of October 1985

[SEAL]

Attest:

DONALD J. QUIGG

Attesting Officer

Commissioner of Patents and
Trademarks—Designate